United States Patent [19]
Hoffmann et al.

[11] 3,957,979
[45] May 18, 1976

[54] PESTICIDAL N-(O-S-DIALKYL(THIONO)-THIOLPHOS-PHORYL)-IMINOFORMIC ACID ALKYL ESTERS

[75] Inventors: Hellmut Hoffmann, Wuppertal-Elberfeld; Ingeborg Hammann, Cologne, both of Germany

[73] Assignee: Bayer Aktiengesellschaft, Leverkusen, Germany

[22] Filed: Feb. 27, 1975

[21] Appl. No.: 553,873

Related U.S. Application Data

[62] Division of Ser. No. 240,282, March 21, 1972, Pat. No. 3,903,207.

[30] Foreign Application Priority Data
Apr. 6, 1971  Germany............................ 2116690

[52] U.S. Cl. ............................................. 424/217
[51] Int. Cl.² ........................................... A01N 9/36
[58] Field of Search ............... 424/45, 217; 260/950

[56] References Cited
UNITED STATES PATENTS

| | | | |
|---|---|---|---|
| 3,281,321 | 10/1966 | Malz et al. | 260/944 X |
| 3,801,679 | 4/1974 | Hoffman et al. | 260/945 |

*Primary Examiner*—Leonard Schenkman
*Attorney, Agent, or Firm*—Burgess, Dinklage & Sprung

[57] ABSTRACT

N-(O,S-dialkyl(thiono)-thiolphosphoryl)-iminoformic acid alkyl esters of the general formula

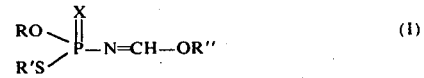

in which
  X is oxygen or sulfur, and
  R, R' and R'' each independently is lower alkyl with 1 to 6 carbon atoms,
which possess insecticidal and acaricidal properties.

10 Claims, No Drawings

PESTICIDAL N-(O-S-DIALKYL(THIONO)-THIOLPHOSPHORYL)-IMINOFORMIC ACID ALKYL ESTERS

This is a division of application Ser. No. 240,282, filed Mar. 21, 1972, now U.S. Pat. No. 3,903,207.

The present invention relates to and has for its objects the provision of particular new N-(O,S-dialkyl (thiono)-thiolphosphoryl)-iminoformic acid alkyl esters which possess insecticidal and acaricidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is known from German Published Specification DAS No. 1,195,750 that N-(O,O-dialkylphosphoryl)-imino-dithiocarbonic acid dialkyl esters, such as N-(O,O-diethylphosphoryl)-imino-dithiocarbonic acid diethyl ester (Compound A) have insecticidal properties.

The present invention provides N-(O,S-dialkyl(thionothiolphosphoryl)-iminoformic acid alkyl esters of the formula $$\begin{array}{c} RO \\ R'S \end{array} \!\!\! \overset{X}{\underset{\|}{P}}\!-\!N\!=\!CH\!-\!OR'' \qquad (I)$$

in which
X is oxygen or sulfur, and
R, R' and R'' each independently is lower alkyl with 1 to 6 carbon atoms.

Preferably R and R' each is a straight chain or branched lower alkyl with 1 to 4 carbon atoms, such as methyl, ethyl, n-propyl, isopropyl, n-butyl, isobutyl, sec.-butyl or tert,-butyl, and R'' is a lower alkyl with 1–3 carbon atoms.

Surprisingly, the compounds according to the invention have a rather better insecticidal, especially systemic and acaricidal activity than the known N-(O,O-dialkylphosphoryl)-iminodithio carbonic acid dialkyl esters of analogous constitution and the same direction of activity. They therefore represent a genuine enrichment of the art.

The invention also provides a process for the production of a N-(O,S-dialkyl-(thiono)-thiolphosphoryl)-imino formic acid alkyl esters of the formula (I) in which an O,S-dialkyl-(thiono)-thiolphosphoric acid ester amide of the formula $$\begin{array}{c} RO \\ R'S \end{array}\!\!\!\overset{X}{\underset{\|}{P}}\!-\!NH_2 \qquad (II)$$

in which
X, R and R' have the meanings stated above,
is reacted with an ortho-formic acid alkyl ester of the formula $$R''O\!-\!\underset{\underset{\displaystyle OR''}{|}}{CH}\!-\!OR'' \qquad (III)$$

in which
R'' has the meaning stated above.

If O,S-dimethylthiolphosphoric acid ester amide and ortho-formic acid ethyl ester are used as starting materials, the reaction course can be represented by the following formula scheme:

$$\underset{(IIa)}{\begin{array}{c} CH_3O \\ CH_3S \end{array}\!\!\!\overset{O}{\underset{\|}{P}}\!-\!NH_2} + \underset{(IIIa)}{\begin{array}{c} C_2H_5O \\ C_2H_5O \end{array}\!\!\!CH\!-\!OC_2H_5} \xrightarrow{-2C_2H_5OH} \underset{(I)}{\begin{array}{c} CH_3O \\ CH_3S \end{array}\!\!\!\overset{O}{\underset{\|}{P}}\!-\!N\!=\!CH\!-\!OC_2H_5} \qquad (IV)$$

Examples of the compounds of formulae (II) and III) include: O,S-dimethyl-, O,S-diethyl-, O,S-di-n-propyl-, O,S-di-isopropyl-, O,S-di-n-butyl-, O,S-di-sec.-butyl-, O,S-di-isobutyl-, O,S-di-tert.-butyl-, O-methyl-S-ethyl-, O-methyl-S-n-propyl-, O-methyl-S-iso-propyl-, O-methyl-S-n-butyl-, O-methyl-S-iso-butyl-, O-methyl-S-tert.-butyl-, O-methyl-S-sec.-butyl-, O-ethyl-S-n-propyl-, O-ethyl-S-isopropyl-, O-ethyl-S-n-butyl-, O-ethyl-S-sec.-btuyl-, O-ethyl-S-iso-butyl-, O-ethyl-S-tert.-butyl-, O-n-propyl-S-n-butyl-, O-n-propyl-S-sec.-butyl-, O-n-propyl-S-tert.-butyl-, O-n-propyl-S-iso-butyl-, O-iso-propyl-S-n-butyl, O-iso-propyl-S-sec.-butyl- and O-iso-propyl-S-tert.-butyl-thiolophosphoric acid ester amide and the corresponding thiono analogues, and the methyl, ethyl or propyl esters orthoformic acid.

The compounds of formula (II) are known from the literature and can be made by known methods, e.g. German Published Specification DAS No. 1,216,835 and Dutch Pat. No. 69 11925. The compounds of formula (III) and methods for their preparation are also known.

The process according to the present invention can be carried out with the use of a solvent, which term includes a mere diluent. Preferably, however, no solvent is used for the reaction.

If desired an acid catalyst may be used, for example p-toluene-sulfonic acid.

The reaction temperatures can be varied over a wide range. In general, the reaction is carried out at about 100°–200°C, preferably about 140°–160°C.

In general, the reaction is carried out at normal pressure.

In carrying out the process, the reactants are preferably brought together in the absence of any solvent, the ortho-formic acid ester being usually used in a 10–20 percent excess. The mixture is boiled under reflux for several hours, in the course of which the alcohol which forms is distilled off. The residue is distilled.

The compounds of the invention are in most cases obtained as colorless or slightly yellow oils which can mostly be distilled without decomposition. If not, they can be freed from volatile impurities by "slight distillation," that is, longer heating to moderately elevated temperatues under reduced pressure. The refractive index is particularly useful for their characterization.

As indicated above, the compounds of the invention are distinguished by outstandng insecticidal and acaricidal effectiveness against crop pests, hygiene pests and pests of stored products. They have a good activity against both sucking and biting insects and mites (Acarina). They are at the same time only slightly phytotoxic and have a 5-fold to 10-fold lower toxicity to warm-blooded animals than do the compounds from which they are derived.

The compounds of the invention can therefore be used successfully as pesticides in crop protection and the protection of stored products as well as in the field of hygiene.

To the sucking insects contemplated herein there belong, in the main, aphids (Aphidae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid *Cryptomyzus korschelti*), the rosy apple aphid (Sappaphis mali), the mealy plum aphid (*Hyalopterus arundinis*) and the cherry black-fly (*Myzus cerasi*); in addition, scales and mealybugs (Coccina), for example the oleander scale (*Aspidiotus hederae*) and the soft scale (*Lecanium hesperidum*) as well as the grape mealybug (*Pseudococcus maritimus*); thrips (Thysanoptera), such as *Hercinothrips femoralis*, and bugs, for example the beet bug (Piesma quadrata), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus;* and the like.

In the case of the biting insects contemplated herein, above all there should be mentioned butterfly caterpillars (Lepidoptera) such as the diamond-back moth (*Plutella maculipennis*), *the gypsy moth (Lymantria dispar)*, the browntail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), *the green oak tortrix moth (Tortrix viriduna*), the fall armyworm (*Laphygma frugiperda*) and cotton worm (*Prodenia litura*), the ermine moth (*Hyponomeuta padella*), the Mediterranean flour moth (*Ephestia kuehniella*) and greater wax moth (Galleria mellonella); and the like.

Also to be classed with the biting insects contemplated herein are beetles (*Coleoptera*), for example the granary weevil (*Sitophilus granarius* = *Calandra granaria*), the Colorado beetle (*Leptinotarsa decemlineata*), the dock beetle (*Gastrophysa viridula*), the mustard beetle (*Phaedon cochleariae* ), the blossom beetle (*Meligethes aeneus*), the raspberry beetle (Byturus tomentosus), the bean weevil (Bruchidius = *Acanthoscelides obtectus*), the leather beetle (*Dermestes frischi*), the khapra beetle (Trogoderma granarium), the flour beetle (*Tribolium castaneum*), the northern corn billbug (Calandra or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (*Agriotes spec.*) and larvae of the cockchafer (*Melolontha melolontha*); cockroaches, such as the German cockroach (*Blattela germanica*), American cockroach (*Periplaneta americana*), Madeira cockroach (*Leucophea*or Rhyparobiamaderae), oriental cockroach (*Blatta orientalis*), the giant cockroach (Blaberus giganteus) and the black giant cockroach (*Blaberus fuscus*) as well as *Henschoutedenia flexivitta;* further, Orthoptera, for example the house cricket (*Acheta domesticus*); termites such as the eastern subterranean termite (*Reticulitermes flavipes*) and Hymenoptera such as ants, for example the garden ant (*Lasius niger*); and the like.

The Diptera contemplated herein essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*); and the like.

With the mites (Acari) contemplated herein there are classed, in particular, the spider mites (Tetranychidae) such as the two-spotted spider mite (*Tetranychus telarius* = *Tetranychus althaeae* or *Tetranychus urticae*) and the European red mite (*Paratetranychus pilosus* = *Panonycus ulmi*), gall mites, for example the black current gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*); and the like.

When applied against hygiene pests and pests of stored products, particularly flies and mosquitoes, the compounds of the invention are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chlorethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicares, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides and acaricides, or rodenticides, fungicides, bactericides, nematocides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10 percent, preferably 0.01–1 percent, by weight of the mixture. Thus, the present invention contemplates over-all compositions which comprises mixtures of a conventional dispersible carrier vehicle such as (1) a dispersible inert finely divided carrier solid, and/or (2) a dispersible carrier liquid such as an inert organic solvent and/or wafer preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95 percent and preferably 0.01–95 percent by weight of the mixture.

The active compounds can also be used in accordance with the well known ultra-low-volume process with good success, i.e. by applying composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100 percent active substance alone, e.g. about 20–100% by weight of the active compound.

Furthermore, the present invention contemplates methods of selectively killing, combating or controlling pests, e.g. insects and acarids, which comprises applying to at least one of correspondingly (a) such insects, (b) such acarids, and (c) the corresponding habitat thereof, i.e. the locus to be protected, a correspondingly combative or toxic amount, i.e. an insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The synthesis, unexpected superiority and outstanding activity of the particular new compounds of the present invention are illustrated, without limitation, by the following examples:

EXAMPLE 1

Myzus test (contact action)

Solvent: 3 parts by weight acetone
Emulsifier: 1 part by weight alkylarylpolyglycol ether To produce a suitable preparation of active compound, 1 part by weight of the active compound is mixed with the stated amount of solvent containing the stated amount of emulsifier and the concentrate is diluted with water to the desired concentration.

Cabbage plants (*Brassica oleracea*) which have been heavily infested with peach aphids (*Myzus persicae*) are sprayed with the preparation of the active compound until dripping wet.

After the specified periods of time, the degree of destruction is determined as a percentage: 100 percent means that all the aphids are killed whereas 0 percent means that none of the aphids are killed.

The active compounds, the concentrations of the active compounds, the evaluation times and the results can be seen from the following Table 1:

Table 1

| Active compounds | (plant-damaging insects) Myzus test | |
|---|---|---|
| | Concentration of active compound in % | Degree of destruction in % after 1 day |
| $(C_2H_5O)_2\overset{O}{\underset{\|\|}{P}}-N=C(SC_2H_5)_2$ (known) | (A) 0.1 | 0 |

Table 1-continued

| Active compounds | | (plant-damaging insects) Myzus test | |
|---|---|---|---|
| | | Concentration of active compound in % | Degree of destruction in % after 1 day |
| $\text{CH}_3\text{O}\diagdown\overset{\text{O}}{\underset{\|}{\text{P}}}-\text{N}=\text{CH}-\text{OC}_2\text{H}_5$ $\text{CH}_3\text{S}\diagup$ | (1) | 0.1 0.01 | 100 |
| $\text{C}_2\text{H}_5\text{O}\diagdown\overset{\text{O}}{\underset{\|}{\text{P}}}-\text{N}=\text{CH}-\text{OC}_2\text{H}_5$ $\text{CH}_3\text{S}\diagup$ | (2) | 0.1 0.01 | 100 99 |
| $\text{CH}_3\text{O}\diagdown\overset{\text{S}}{\underset{\|}{\text{P}}}-\text{N}=\text{CH}-\text{OC}_2\text{H}_5$ $\text{CH}_3\text{S}\diagup$ | (3) | 0.1 0.01 | 100 20 |
| $\text{CH}_3\text{O}\diagdown\overset{\text{O}}{\underset{\|}{\text{P}}}-\text{N}=\text{CH}-\text{OCH}_3$ $\text{CH}_3\text{S}\diagup$ | (4) | 0.1 0.01 | 100 90 |
| $\text{CH}_3\text{O}\diagdown\overset{\text{S}}{\underset{\|}{\text{P}}}-\text{N}=\text{CH}-\text{OCH}_3$ $\text{CH}_3\text{S}\diagup$ | (6) | 0.1 0.01 | 100 75 |
| $\text{C}_2\text{H}_5\text{O}\diagdown\overset{\text{O}}{\underset{\|}{\text{P}}}-\text{N}=\text{CH}-\text{OCH}_3$ $\text{CH}_3\text{S}\diagup$ | (5) | 0.1 0.01 | 100 95 |

EXAMPLE 2

Doralis test (systemic action)

Solvent: 3 parts by weight acetone
Emulsifier: 1 part by weight alkylarylpolyglycol ether To produce a suitable preparation of active compound, 1 part by weight of the active compound is mixed with the stated amount of solvent containing the stated amount of emulsifier, and the concentrate is diluted with water to the desired concentration.

Bean plants (*Vicia faba*) which have been heavily infested with the bean aphid (*Doralis fabae*) are watered with the preparation of the active compound so that the preparation of active compound penetrates into the soil without wetting the leaves of the bean plants. The active compound is taken up by the bean plants from the soil and thus reaches the infested leaves.

After the specified period of time, the degree of destruction is determined as a percentage. 100 percent means that all the aphids are killed; 0 percent means that none of the aphids are killed.

The active compounds, the concentrations of the active compounds, the evaluation time and the results can be seen from the following Table 2:

Table 2

| Active compounds | | (plant-damaging insects) Doralis test (syst. action) | |
|---|---|---|---|
| | | Concentration of active compound in % | Degree of destruction in % after 4 days |
| $(\text{C}_2\text{H}_5\text{O})_2\overset{\text{O}}{\underset{\|}{\text{P}}}-\text{N}=\text{C}(\text{SC}_2\text{H}_5)_2$ (known) | (A) | 0.1 | 0 |
| $\text{CH}_3\text{O}\diagdown\overset{\text{O}}{\underset{\|}{\text{P}}}-\text{N}=\text{CH}-\text{OC}_2\text{H}_5$ $\text{CH}_3\text{S}\diagup$ | (1) | 0.1 0.01 | 100 100 |
| $\text{C}_2\text{H}_5\text{O}\diagdown\overset{\text{O}}{\underset{\|}{\text{P}}}-\text{N}=\text{CH}-\text{OC}_2\text{H}_5$ $\text{CH}_3\text{S}\diagup$ | (2) | 0.1 0.01 0.001 | 100 100 99 |
| $\text{CH}_3\text{O}\diagdown\overset{\text{O}}{\underset{\|}{\text{P}}}-\text{N}=\text{CH}-\text{OCH}_3$ $\text{CH}_3\text{S}\diagup$ | (4) | 0.1 0.01 0.001 | 100 100 90 |
| $\text{C}_2\text{H}_5\text{O}\diagdown\overset{\text{O}}{\underset{\|}{\text{P}}}-\text{N}=\text{CH}-\text{OCH}_3$ $\text{CH}_3\text{S}\diagup$ | (5) | 0.1 0.01 0.001 | 100 100 100 |

EXAMPLE 3

Tetranychus test/resistant

Solvent: 3 parts by weight acetone
Emulsifier: 1 part by weight alkylarylpolyglycol ether To produce a suitable preparation of active compound, 1 part by weight of the active compound is mixed with the stated amount of solvent contaning the stated amount of emulsifier and the concentrate so obtained is diluted with water to the desired concentration.

Bean plants (*Phaseolus vulgaris*), which have a height of approximately 10–30 cm., are sprayed with the preparation of the active compound until dripping wet. These bean plants are heavily infested with spider mites (*Tetranychus urticae*) in all stages of development.

After the specified periods of time, the effectiveness of the preparation of active compound is determined by counting the dead mites. The degree of destruction thus obtained is expressed as a percentage: 100 percent means that all the spider mites are killed whereas 0 percent means that none of the spider mites are killed.

The active compounds, the concentrations of the active compounds, the evaluation times and the results can be seen from the following Table 3:

Table 3

| Active compounds | | (plant-damaging mites) Tetranychus test (resistant) Concentration of active compound in % | Degree of destruction in % after 2 days |
|---|---|---|---|
| $(C_2H_5O)_2\overset{O}{\underset{\|}{P}}-N=C(SC_2H_5)_2$ (known) | (A) | 0.1 | 0 |
| $\begin{array}{c}CH_3O\\CH_3S\end{array}\!\!>\!\!\overset{O}{\underset{\|}{P}}-N=CH-OC_2H_5$ | (1) | 0.1 | 100 100 |
| $\begin{array}{c}C_2H_5O\\CH_3S\end{array}\!\!>\!\!\overset{O}{\underset{\|}{P}}-N=CH-OC_2H_5$ | (2) | 0.1 | 98 |
| $\begin{array}{c}CH_3O\\CH_3S\end{array}\!\!>\!\!\overset{O}{\underset{\|}{P}}-N=CH-OCH_3$ | (4) | 0.1 0.01 | 100 30 |
| $\begin{array}{c}C_2H_5O\\CH_3S\end{array}\!\!>\!\!\overset{O}{\underset{\|}{P}}-N=CH-OCH_3$ | (5) | 0.1 | 95 |

The following further examples are set forth to illustrate, without limitaton, te process for producing the active compounds according to the present invention.

EXAMPLE 4

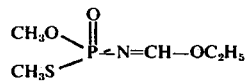  (1)

71 g (0.5 mole) of O-methyl-S-methyl-thiolphosphoric acid ester amide are heated to the boil under reflux for 4 hours with 92 g of orthoformic acid ethyl ester. Subsequently, the alcohol formed is distilled off and the residue is distilled. There are obtained 56 g (57 percent of theory) of the desired N-(O,S-dmethylthiolphosphoryl)-iminoformic acid ethyl ester of the boiling point 84°C/0.01 mm Hg and the refractive index $n_D^{22}=1.4892$. $LD_{50}$ rat per os approximately 200 mg/kg.

EXAMPLE 5

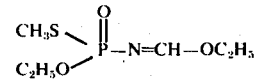  (2)

47 g (0.3 mole) of O-ethyl-S-methyl-thiolphosphoric acid ester amide and 55 g orthformic acid ethyl ester are heated to 150°C for 4 hours; the alcohol forming is distilled off simultaneously. The residue is distilled and there are obtained 52 g (82% of theory) of the desired N-(O-ethyl-S-methyl-thiolphosphoryl)-iminoformic acid ethyl ester of the boiling point 88°C/0.01 mm Hg and the refractive index $n_D^{27}=1.4802$. $LD_{50}$ rat per os 50 mg/kg.

EXAMPLES 6–10

Analogously to the compounds described above, there are prepared:

| Constitution | | Physical properties | Yield % of theory |
|---|---|---|---|
| $\begin{array}{c}CH_3S\\CH_3O\end{array}\!\!>\!\!\overset{S}{\underset{\|}{P}}-N=CH-OC_2H_5$ | (3) | $n_D^{24}=1.5417$ b.p.: 84°C/0.01 mm Hg | 94 % |
| $\begin{array}{c}CH_3S\\CH_3O\end{array}\!\!>\!\!\overset{O}{\underset{\|}{P}}-N=CH-OCH_3$ | (4) | $n_D^{24}=1.5019$ b.p.: 84°C/0.01 mm Hg | 70 % |
| $\begin{array}{c}CH_3\\C_2H_5O\end{array}\!\!>\!\!\overset{O}{\underset{\|}{P}}-N=CH-OCH_3$ | (5) | $n_D^{23}=1.4892$ b.p.: 86°C/0.01 mm Hg | 43 % |
| $\begin{array}{c}CH_3S\\CH_3O\end{array}\!\!>\!\!\overset{S}{\underset{\|}{P}}-N=CH-OCH_3$ | (6) | $n_D^{25}=1.5530$ b.p.: 78°C/0.01 mm Hg | 85 % |

It will be appreciated that the instant specification and examples are set forth by way of illustration and not limitation, and that various modifications and changes may be made without departing from the spirit and scope of the present invention.

What is claimed is:

1. A method of combating insect or acarid pests which comprises applying to the pests or a habitat thereof an insecticidally or acaricidally effective amount of a compound of the formula

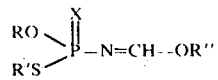

in which
X is oxygen or sulfur, and
R, R' and R'' each independently is alkyl with 1 to 6 carbon atoms.

2. The method according to claim 1 in which R and R' each has 1 to 4 carbon atoms and R'' has 1 to 3 carbon atoms.

3. The method according to claim 1 wherein the compound is N-(O,S-dimethylthiolphosphoryl)-iminoformic acid ethyl ester of the formula

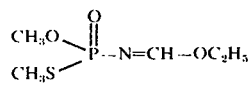 (1)

4. The method according to claim 1 wherein the compounds is N-(O-ethyl-S-methylthiolphosphoryl)-iminoformic acid ethyl ester of the formula

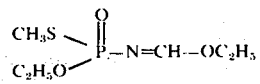 (2)

5. The method according to claim 1 wherein the compound is N-(O,S-dimethylthionothiolphosphoryl)-iminoformic acid ethyl ester of the formula

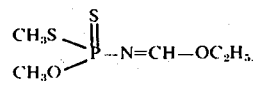 (3)

6. The method according to claim 1 wherein the compound is N-(O,S-dimethylthiolphosphoryl)-iminoformic acid methyl ester of the formula

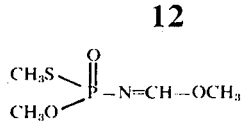 (4)

7. The method according to claim 1 wherein the compound is N-(O-ethyl-S-methylthiolphosphoryl)-iminoformic acid methyl ester of the formula

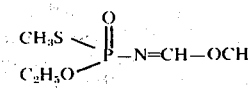 (5)

8. The method according to claim 1 wherein the compound is N-(O,S-dimethylthionothiolphosphoryl)-iminoformic acid methyl ester of the formula

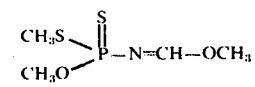 (6)

9. An insecticidal or acaricidal composition containing an insecticidally or acaricidally effective amount of a compound of the formula

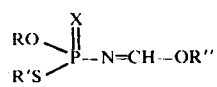

in which
X is oxygen or sulphur, and
R, R' and R'' each independently is alkyl with 1 to 6 carbon atoms,
in admixture with a diluent.

10. The composition according to claim 9 in which the compound is:
N-(O,S-dimethylthiolphosphoryl)-iminoformic acid ethyl ester,
N-(O-ethyl-S-methylthiolphosphoryl)-iminoformic acid ethyl ester,
N-(O,S-dimethylthionothiolphosphoryl)-iminoformic acid ethyl ester,
N-(O,S-dimethylthiolphosphoryl)-iminoformic acid methyl ester,
N-(O-ethyl-S-methylthiolphosphoryl)-iminoformic acid methyl ester, or
N-(O,S-dimethylthionothiolphosphoryl)-iminoformic acid methyl ester.

* * * * *

UNITED STATES PATENT OFFICE
CERTIFICATE OF CORRECTION

Patent No. 3,957,979  Dated May 18, 1976

Inventor(s) Hoffmann et al

It is certified that error appears in the above-identified patent and that said Letters Patent are hereby corrected as shown below:

Col. 2, line 35, after "esters" insert -- of --.
Col. 3, line 40, correct spelling of "viridana".
Col. 3, lines 65,66, cancel "Leucopheaor Rhyparobiamaderae" and substitute -- Leucophaea or Rhyparobia maderae--.
Col. 4, line 23, correct spelling of "Panonychus".
Col. 5, line 8, corret spelling of "silicates".
Col. 5, line 46, cancel "wafer" and substitute -- water --.

Col.8, line 65, correct spelling of "containing".
Col. 9, formula (1) - second column of numbers, cancel "100", second occurrence.
Col. 9, line 39, cancel "te" and substitute -- the --.
Col. 10, formula (5), change "$CH_3\backslash$" to -- $CH_3S\backslash$ --.
Col. 11, line 3, correct spelling of "limitation".

Signed and Sealed this

Sixteenth Day of May 1978

[SEAL]

Attest:

RUTH C. MASON
Attesting Officer

LUTRELLE F. PARKER
Acting Commissioner of Patents and Trademarks